(12) United States Patent
Tsurushima et al.

(10) Patent No.: US 10,369,115 B2
(45) Date of Patent: Aug. 6, 2019

(54) CATAPLASM AND METHOD FOR PRODUCING THE SAME

(71) Applicant: HISAMITSU PHARMACEUTICAL CO., INC., Tosu-shi, Saga (JP)

(72) Inventors: Keiichiro Tsurushima, Tosu (JP); Yasuhisa Kose, Tosu (JP); Shinji Yamasoto, Tosu (JP); Seiichiro Tsuru, Tosu (JP); Takaaki Yoshinaga, Tosu (JP)

(73) Assignee: HISAMITSU PHARMACEUTICAL CO., LTD., Tosu-Shi, Saga (JP)

( * ) Notice: Subject to any disclaimer, the term of this patent is extended or adjusted under 35 U.S.C. 154(b) by 0 days.

(21) Appl. No.: 14/913,455

(22) PCT Filed: Aug. 21, 2014

(86) PCT No.: PCT/JP2014/071940
§ 371 (c)(1),
(2) Date: Feb. 22, 2016

(87) PCT Pub. No.: WO2015/025935
PCT Pub. Date: Feb. 26, 2015

(65) Prior Publication Data
US 2016/0206569 A1 Jul. 21, 2016

(30) Foreign Application Priority Data

Aug. 23, 2013 (JP) .................................. 2013-173664

(51) Int. Cl.
| | | |
|---|---|---|
| A61K 9/70 | (2006.01) |
| A61L 15/22 | (2006.01) |
| A61L 15/58 | (2006.01) |
| A61L 15/60 | (2006.01) |
| C08L 71/00 | (2006.01) |
| C08F 220/14 | (2006.01) |
| C08L 33/02 | (2006.01) |

(52) U.S. Cl.
CPC .......... A61K 9/7061 (2013.01); A61L 15/225 (2013.01); A61L 15/585 (2013.01); A61L 15/60 (2013.01); C08F 220/14 (2013.01); C08L 33/02 (2013.01); C08L 71/00 (2013.01)

(58) Field of Classification Search
None
See application file for complete search history.

(56) References Cited

U.S. PATENT DOCUMENTS

| 5,176,916 A | 1/1993 | Yamanaka et al. |
| 5,362,497 A | 11/1994 | Yamada et al. |
| 5,776,484 A | 7/1998 | Sasaki et al. |
| 2007/0148216 A1 | 6/2007 | Yoshitake et al. |

FOREIGN PATENT DOCUMENTS

| EP | 0399432 A2 | 11/1990 | |
| EP | 0452837 A2 | 10/1991 | |
| JP | S55-122714 A | 9/1980 | |
| JP | 57181020 A | 11/1982 | |
| JP | 372416 A | 3/1991 | |
| JP | 41127 A | 1/1992 | |
| JP | 8119859 A | 5/1996 | |
| JP | 09208462 A | 8/1997 | |
| JP | 2002104954 A | 4/2002 | |
| JP | 2002104957 A | 4/2002 | |
| JP | 2004067562 A | 3/2004 | |
| JP | 2004256396 A | 9/2004 | |
| JP | 2011140501 A | 7/2011 | |
| JP | WO 2012102242 A1 * | 8/2012 | ........... A61K 9/7038 |
| TW | 201236701 A | 9/2012 | |
| WO | 2005/023307 A1 | 3/2005 | |
| WO | 2006090782 A1 | 8/2006 | |
| WO | 2012/102242 A1 | 8/2012 | |
| WO | 2013012000 A1 | 1/2013 | |

OTHER PUBLICATIONS

English translation of WO2012102242 retrieved from WIPO on May 1, 2017.*
International Preliminary Report on Patentability for WO Patent Application No. PCT/JP2014/071940 dated Mar. 3, 2016.
Supplementary European Search Report dated Mar. 17, 2017 corresponding to European application No. EP14837171.
International Search Report dated Nov. 18, 2014 corresponding to International application No. PCT/JP2014/071940.

* cited by examiner

*Primary Examiner* — Jessica Worsham
(74) *Attorney, Agent, or Firm* — Nath, Goldberg & Meyer; Tanya E. Harkins; Joshua B. Goldberg (57) ABSTRACT

A gel patch comprising a plaster layer on a support, the plaster layer comprising a mixture of at least a neutralized polyacrylic acid, a poly(methyl acrylate/2-ethylhexyl acrylate) emulsion, and water, wherein the poly(methyl acrylate/2-ethylhexyl acrylate) emulsion is an emulsion having an evaporation residue of 57 to 61% by heating at or above the boiling point of the medium and is present in an amount of at least 2.5 times and preferably at least 3 times the mass of the neutralized polyacrylic acid.

18 Claims, 6 Drawing Sheets

CATAPLASM AND METHOD FOR PRODUCING THE SAME

This is a National Phase Application filed under 35 U.S.C. 371 as a national stage of PCT/JP2014/071940, filed Aug. 21, 2014, an application claiming the benefit of Japanese Application No. 2013-173664, filed Aug. 23, 2013, the content of each of which is hereby incorporated by reference in its entirety.

TECHNICAL FIELD

The present invention relates to a gel patch and to a method for producing it.

BACKGROUND ART

Gel patches are a type of poultice produced by coating a plaster containing a drug onto a support such as a fabric, and they generally include a large amount of water, have a thick plaster, and have low skin irritation. However, the adhesive force is usually reduced with the passage of time after the gel patch has been applied, and therefore ways of minimizing reduction in adhesive force have been studied, as described in PTLs 1 and 2, for example.

CITATION LIST

Patent Literature

[PTL 1] JP HEI 9-208462 A
[PTL 2] WO 2006/090782 A

SUMMARY OF INVENTION

Technical Problem

In the gel patches described in PTLs 1 and 2, the adhesive force is often inadequate when the thickness of the plaster has been reduced or after elapse of long time periods. Furthermore, in the water-including external-use poultice that contains partially neutralized polyacrylic acid and sodium polyacrylate, described in PTL 2, the pH is high and the moldability, shape retention and skin irritability of the external-use poultice remain as problems. It is therefore an object of the present invention to provide a gel patch having sufficient adhesive force even when the amount of water in the gel patch has been reduced after the passage of time.

Solution to Problem

The present invention provides a gel patch comprising a plaster layer on a support: the plaster layer comprising a mixture of at least neutralized polyacrylic acid, a poly(methyl acrylate/2-ethylhexyl acrylate) emulsion (hereunder also referred to as "methyl acrylate/2-ethylhexyl acrylate copolymer resin emulsion"), and water; wherein the poly(methyl acrylate/2-ethylhexyl acrylate) emulsion is present in an amount of at least 2.5 times and preferably at least 3 times greater by mass than the neutralized polyacrylic acid.

The gel patch of the invention has a plaster layer formed from at least water, a neutralized polyacrylic acid and a poly(methyl acrylate/2-ethylhexyl acrylate) emulsion, the poly(methyl acrylate/2-ethylhexyl acrylate) emulsion being at least 2.5 times and preferably at least 3 times greater by mass than the neutralized polyacrylic acid, whereby adequate adhesive force can be maintained even after elapse of a long period of time following application.

The poly(methyl acrylate/2-ethylhexyl acrylate) emulsion is preferably an emulsion containing poly(oxyethylene)nonylphenyl ether. Most preferably, the emulsion uses a poly(oxyethylene)nonylphenyl ether as a surfactant or protective colloid. Using such an emulsion will increase the ability to maintain adhesive force.

The polyacrylate is preferably partially neutralized polyacrylic acid. By using partially neutralized polyacrylic acid instead of fully neutralized polyacrylic acid as the polyacrylate, it is possible to increase both the initial adhesion and the adhesion after elapse of long periods following application.

The water present in the plaster layer is preferably greater by mass than the poly(methyl acrylate/2-ethylhexyl acrylate) emulsion.

The water present in the plaster layer is preferably at least 4 times greater by mass than the neutralized polyacrylic acid.

The plaster layer is preferably obtained by mixing the neutralized polyacrylic acid, poly(methyl acrylate/2-ethylhexyl acrylate) emulsion and water in a mass ratio of neutralized polyacrylic acid:poly(methyl acrylate/2-ethylhexyl acrylate) emulsion:water=1:2.5-7:5-16, and more preferably it is obtained by mixing the neutralized polyacrylic acid, poly(methyl acrylate/2-ethylhexyl acrylate) emulsion and water in a mass ratio of neutralized polyacrylic acid:poly(methyl acrylate/2-ethylhexyl acrylate) emulsion:water=1:2.5-7:7-16. Mixing in this ratio range will further increase the ability to maintain adhesive force.

The water content of the plaster layer is preferably 20 to 60 mass %, based on the total mass of the plaster layer. If the water content is within this range, it will be easier to obtain synergistic adhesive force by the adhesive force of the neutralized polyacrylic acid and the adhesive force of the poly(methyl acrylate/2-ethylhexyl acrylate).

The content of the neutralized polyacrylic acid in the plaster layer is preferably 1 to 6 mass %, based on the total mass of the plaster layer. If the content of the neutralized polyacrylic acid is within this range, it will be possible to obtain adequate adhesive force when the water content is high, and to reduce the hardness of the gel patch. Moreover, by lowering the hardness of the gel patch, adhesiveness with the skin is increased and the adhesive force is further increased.

The plaster layer preferably further contains polyacrylic acid. By containing polyacrylic acid, a high ability to maintain adhesive force is retained, and the shape retention of the gel patch is increased.

The mass of the plaster layer may be 214 to 1000 g/m$^2$, 400 to 1000 g/m$^2$ or even 400 to 650 g/m$^2$, for example. In a conventional gel patch, a low weight for the plaster layer tends to lower the water content and reduce the adhesive force. According to the invention, however, adequate adhesive force is maintained even after elapse of long periods, even when the mass of the plaster layer is within the relatively low range mentioned above.

In a gel patch of the invention, the adhesive force is based on the poly(methyl acrylate/2-ethylhexyl acrylate) in the poly(methyl acrylate/2-ethylhexyl acrylate) emulsion, and the neutralized polyacrylic acid, the adhesive force when a water content of a plaster layer is 30 mass % or higher being greater with the neutralized polyacrylic acid than the poly(methyl acrylate/2-ethylhexyl acrylate), and the adhesive force with a plaster layer water content of less than 25 mass % being greater with the poly(methyl acrylate/2-ethylhexyl acrylate) than the neutralized polyacrylic acid, such that adequate adhesive force is exhibited even when the water content of the gel patch has been reduced with the passage of time.

The present invention also provides a method for producing a gel patch comprising a plaster layer on a support, wherein the pressure-sensitive adhesive force is maintained even with reduced water content. That is, if the plaster layer is obtained comprising at least, in addition to water and a neutralized polyacrylic acid, a poly(methyl acrylate/2-ethylhexyl acrylate) emulsion in an amount of at least 2.5 times the mass of the neutralized polyacrylic acid, then the resulting gel patch will maintain its pressure-sensitive adhesive force even with reduction in the water content.

Advantageous Effects of Invention

According to the gel patch of the invention, it is possible to maintain adequate adhesive force even when a long period of time has elapsed following application and the amount of the water in the plaster layer has been reduced.

DESCRIPTION OF EMBODIMENTS

A preferred embodiment of the invention will now be described in detail.

The gel patch of the embodiment comprises a plaster layer on a support. The support may be one that can support a water-containing plaster obtained by mixing at least a neutralized polyacrylic acid, a poly(methyl acrylate/2-ethylhexyl acrylate) emulsion, and water. Examples of such supports include woven fabrics, nonwoven fabrics, resin films, foamed sheets and paper sheets, with examples of woven fabrics including knitted fabrics. When a woven fabric, nonwoven fabric or resin film is used as the support, the material may be, for example, a polyolefin such as polyethylene, polypropylene or polybutylene, a polyester such as polyethylene terephthalate, or rayon, polyurethane or cotton, any of which may be used alone or in combinations of two or more. The support is more preferably a polyester.

The support is preferably a nonwoven fabric or woven fabric, and most preferably a nonwoven fabric or woven fabric having a prescribed elongation recovery rate. The elongation recovery rate referred to here is the value measured according to "JIS L 1096: Testing Methods for Woven and Knitted Fabrics". Using a nonwoven fabric or woven fabric having such an elongation recovery rate is preferred because, when applied to moving parts such as joints, the support will stretch in response to movement of the site of application.

When the support is a nonwoven fabric, the load at 50% elongation is preferably 1 to 5 N/2.5 cm in the longitudinal direction (long axis direction) and 0.1 to 3 N/2.5 cm in the transverse direction (short axis direction). Furthermore, the 50% elongation recovery rate is, for example, 60 to 99%, preferably 65 to 95% and more preferably 70 to 90%. A desirable basis weight for the support is, for example, 80 to 120 g/m$^2$, and preferably 90 to 110 g/m$^2$. A desirable thickness for the support is, for example, 0.5 to 2 mm. Also, the bending resistance of the support (where the bending resistance measuring method is based on the 45° cantilever method of JIS L 1096) may be, for example, 20 to 40 mm in the longitudinal direction (long axis direction) and 10 to 35 mm in the transverse direction (short axis direction), and is preferably 25 to 35 mm in the longitudinal direction (long axis direction) and 15 to 30 mm in the transverse direction (short axis direction).

When a woven fabric, and especially a knitted fabric is used as the support for the invention, this may include knitted fabrics processed into a sheet with assembly by circular knit, warp knit, weft knit or the like as the stitch form. Examples of preferred knitted fabrics include knitted fabrics comprising combinations of one or more materials from among polyester-based, nylon-based, polypropylene-based and rayon-based materials, of which knitted polyester-based fabrics comprising polyethylene terephthalate are more preferred as they have low interaction with drugs.

When the support is a woven fabric, the load at 50% elongation is preferably 1 to 5 N/2.5 cm in the longitudinal direction (long axis direction) and 0.1 to 3 N/2.5 cm in the transverse direction (short axis direction). Furthermore, the 50% elongation recovery rate is, for example, 60 to 99%, preferably 65 to 95% and more preferably 70 to 90%. Also, the bending resistance of the support may be, for example, 10 to 30 mm in the longitudinal direction (long axis direction) and 10 to 30 mm in the transverse direction (short axis direction), and is preferably 15 to 25 mm in the longitudinal direction (long axis direction) and 15 to 25 mm in the transverse direction (short axis direction).

When a water-containing plaster is spread out onto a woven fabric, the water often seeps in through the mesh of the woven fabric, but if the basis weight of a polyethylene terephthalate woven fabric is 80 to 150 g/m$^2$, the water in the plaster will tend to spread without seeping through the mesh of the woven fabric, helping to maintain anchorage between the woven fabric and the plaster.

In addition, a polyethylene terephthalate woven fabric preferably has a modulus of 2 to 12 N/5 cm in the longitudinal direction (long axis direction) and a modulus of 2 to 8 N/5 cm in the transverse direction (short axis direction) (where the modulus measuring method is according to JIS L 1018). With a modulus of lower than 2 N/5 cm, the woven fabric may elongate when the plaster is coated, causing the pressure-sensitive adhesive to penetrate into the mesh and potentially reducing the function of the gel patch. Furthermore, if the modulus is higher than 12 N/5 cm (longitudinal direction) or 8 N/5 cm (transverse direction), the stretchability may be impaired, potentially impeding the ability to follow stretching of the skin when it is applied to curved sections.

Spreading of the plaster of the invention onto such a woven fabric, and especially knitted fabric, will allow attachment for longer periods.

The plaster layer composing the gel patch is made of a water-containing plaster that is obtainable by mixing at least a neutralized polyacrylic acid, a poly(methyl acrylate/2-ethylhexyl acrylate) emulsion, and water.

The neutralized polyacrylic acid may be a fully neutralized polyacrylic acid or a partially neutralized polyacrylic acid, or a mixture thereof. The neutralized polyacrylic acid may also be a polyacrylic acid salt, which may be a sodium salt, potassium salt, calcium salt, ammonium salt or the like.

The neutralized polyacrylic acid is preferably a partially neutralized polyacrylic acid, since the initial adhesive force and the adhesive force over time will both be increased. The partially neutralized polyacrylic acid has a structural unit from acrylic acid and a structural unit from an acrylate in any desired proportion in a single polymer chain. The partially neutralized polyacrylic acid used is preferably one having neutralization of 50 mol % of the carboxy groups in one polymer chain.

The content of the neutralized polyacrylic acid in the plaster layer is preferably 1 to 6 mass %, and more preferably 2 to 6 mass %, based on the total mass of the plaster layer. If the content of the neutralized polyacrylic acid is 1 mass % or greater, it will be possible to obtain adequate adhesive force for the neutralized polyacrylic acid, and if the content of the neutralized polyacrylic acid is no greater than 6 mass %, the moldability and shape retention of the plaster layer will be improved.

The poly(methyl acrylate/2-ethylhexyl acrylate) emulsion (methyl acrylate/2-ethylhexyl acrylate copolymer resin emulsion) composing the plaster layer is preferably an aqueous emulsion including water as the medium. The poly(methyl acrylate/2-ethylhexyl acrylate) emulsion is also preferably an emulsion using polyoxyethylene nonylphenyl ether as a surfactant or protective colloid. Also preferably, it comprises 57 to 61% of an evaporation residue (nonvolatile component) obtained by heating at or above the boiling point of the medium (for example, at 105° C. for 3 hours). One such emulsion is NIKASOL TS-620 (trade name of Nippon Carbide Industries Co., Inc.). According to Japanese Pharmaceutical Excipients (2013), drying NIKASOL TS-620 at 105° C. for 3 hours following evaporation to dryness on a water bath yields an evaporation residue of 57 to 61%.

The content of the poly(methyl acrylate/2-ethylhexyl acrylate) emulsion in the plaster layer is 5 to 25 mass %, preferably 10 to 20 mass %, more preferably 10 to 18 mass % and even more preferably 6 to 22 mass %, based on the total mass of the plaster layer.

The water content in the plaster layer is preferably 20 to 60 mass %, and more preferably 25 to 50 mass %, based on the total mass of the plaster layer. If the water content is 20 to 60 mass %, the adhesive force of the polyacrylate and the poly(methyl acrylate/2-ethylhexyl acrylate) emulsion will be adequately exhibited even when water has evaporated during application, and it will be possible to further increase the adhesiveness onto skin.

The poly(methyl acrylate/2-ethylhexyl acrylate) emulsion in the plaster layer is preferably at least 2.5 times, more preferably at least 2.7 times and more preferably at least 3 times greater by mass than the neutralized polyacrylic acid. The mass of the poly(methyl acrylate/2-ethylhexyl acrylate) emulsion in the plaster layer is preferably no greater than 10 times, more preferably no greater than 7 times and even more preferably no greater than 5 times the mass of the neutralized polyacrylic acid.

The water in the plaster layer is preferably at least equal to, more preferably at least 1.5 times and even more preferably at least 2 times greater by mass than the poly(methyl acrylate/2-ethylhexyl acrylate) emulsion. The mass of water in the plaster layer is also preferably no greater than 50 times, more preferably no greater than 20 times and even more preferably no greater than 7 times the mass of the poly(methyl acrylate/2-ethylhexyl acrylate) emulsion.

The water in the plaster layer is preferably at least 4 times, more preferably at least 5 times and even more preferably at least 6 times greater by mass than the neutralized polyacrylic acid. The mass of water in the plaster layer is also preferably no greater than 20 times and more preferably no greater than 15 times the mass of the neutralized polyacrylic acid.

The plaster layer is preferably obtained by mixing the neutralized polyacrylic acid, poly(methyl acrylate/2-ethylhexyl acrylate) emulsion and water to a mass ratio of neutralized polyacrylic acid:poly(methyl acrylate/2-ethylhexyl acrylate) emulsion:water=1:2.5-7:7-16. The proportion is more preferably 1:3-5:7-12. Such a proportion will result in a more notable effect of the invention of maintaining adhesive force.

Since a gel patch having this construction undergoes evaporation of water with the passage of time, and the poly(methyl acrylate/2-ethylhexyl acrylate) exhibits adhesive force even when the water content is less than 25 mass %, it is possible to maintain adequate adhesive force for the gel patch as a whole.

The plaster layer may also contain a drug in addition to the essential components mentioned above. Such drugs need only have percutaneous absorption properties, and examples thereof include non-steroidal anti-inflammatory drugs such as felbinac, flurbiprofen, diclofenac, diclofenac sodium, methyl salicylate, glycol salicylate, indomethacin and ketoprofen, or their esters, anti-histamine drugs such as diphenhydramine, analgesics such as aspirin, acetaminophen, ibuprofen and loxoprofen sodium, local anesthetics such as lidocaine, muscle relaxants such as suxamethonium chloride, antifungal agents such as clotrimazole, antihypertensive drugs such as clonidine, vasodilators such as nitroglycerin and isosorbide nitrate, vitamins such as vitamin A, vitamin E (tocopherol), tocopherol acetate, vitamin K, octotiamine and riboflavin butyrate, prostaglandins, scopolamine, fentanyl, l-menthol, capsicum extract and vanillylamide nonylate.

The plaster layer may also include fruit-derived components such as rose fruit extract, orange extract, orange fruit juice, raspberry extract, kiwi extract, cucumber extract, *gardenia* extract, grapefruit extract, hawthorn extract, Japanese pepper extract, whitethorn extract, common juniper extract, jujube extract, *lansium domesticum* extract, tomato extract, grape extract, *luffa* extract, lime fruit juice, apple extract, apple fruit juice, lemon extract and lemon fruit juice, water-soluble placenta extract, allantoin, lecithin, amino acids, kojic acid, proteins, saccharides, hormones, placenta extract, and components extracted from various galenicals such as aloe and liquorice.

Examples of other components that may be added to the plaster layer include ashitaba extract, avocado extract, sweet *hydrangea* extract, althea extract, *arnica* extract, ginkgo extract, fennel extract, turmeric extract, oolong tea extract, scutellaria root extract, phellodendron bark extract, barley extract, watercress extract, sea weed extract, hydrolyzable elastin, hydrolyzed wheat flour, hydrolyzed silk, *chamomilla* extract, *Artemisia capillaris* extract, liquorice extract, *Hibiscus sabdariffa* extract, guanosine, kuma bamboo grass extract, walnut extract, *clematis* extract, yeast extract, burdock extract, comfrey extract, cowberry extract, bupleurum root extract, umbilical cord extract, *salvia* extract, soapwort extract, bamboo grass extract, hawthorn extract, shiitake extract, rehmannia root extract, lithospermum root extract, linden extract, meadowsweet extract, calamus extract, white birch extract, common horsetail extract, honeysuckle extract, common ivy extract, whitethorn extract, elder extract, yarrow extract, peppermint extract, mallow extract, swertia extract, jujube extract, thyme extract, clove extract, Cogon Grass extract, citrus unshiu extract, orange peel extract, dokudami extract, natto extract, *ginseng* extract, bramble extract, *hibiscus* extract, ophiopogon tuber extract, parsley extract, honey, *Parietaria judaica* extract, isodon *japonicus* extract, bisabolol, coltsfoot extract, butterbur extract, hoelen extract, butcher's broom extract, propolis, peppermint extract, Miquel's linden extract, hop extract, pine extract, common horse-chestnut extract, Asian skunk cabbage extract, Indian soapberry extract, peach leaf extract, cornflower extract, *eucalyptus* extract, yuzu extract, Japanese mugwort extract, lavender extract, lettuce extract, Chinese milkvetch extract, rose extract, rosemary extract, Roman chamomile extract and royal jelly extract.

The plaster layer may further contain polyacrylic acid. The content of the polyacrylic acid is preferably 1 to 5 mass %, based on the total mass of the plaster layer. If the content of the polyacrylic acid is at least 1 mass %, the moldability and shape retention of the plaster layer will be improved. If the content of the polyacrylic acid is no greater than 5 mass %, it will be difficult to increase the hardness of the plaster layer, and the adhesiveness on skin will increase.

The pH of the plaster layer is preferably 4 to 8 and more preferably 4.5 to 6. If the pH is 4 or higher the irritation on the skin will be reduced, and if the pH is no higher than 8, the moldability and shape retention of the gel patch can be improved. Seepage can occur during formation of the plaster layer, particularly when the support is a woven fabric and especially a knitted fabric, and such seepage will tend to be suppressed when the pH is 5 to 6.5. The pH can be measured, for example, according to the general pH measuring method of the Japanese Pharmacopoeia, using a glass composite electrode, with the sample diluted 20-fold with purified water.

Other components may also be added to the plaster layer, such as water-soluble polymers, dissolving aids, humectants, fresheners, stabilizers, inorganic powders, coloring agents, flavors and pH regulators.

The water-soluble polymer is not particularly restricted so long as it can retain water in the gel patch, and any one commonly known to those skilled in the art may be used. Examples of water-soluble polymers include gelatin, polyvinyl alcohol, polyvinylpyrrolidone, sodium alginate, hydroxypropyl cellulose, carboxymethyl cellulose sodium (carmellose sodium), methyl cellulose and carrageenan, any of which may be used alone, or two or more of which may be used in combination. Preferred as water-soluble polymers are carmellose sodium, gelatin and polyvinyl alcohol.

The content of the water-soluble polymer is preferably 3 to 10 mass %, based on the mass of the plaster layer.

The dissolving aid is not particularly restricted so long as it can dissolve the drug, and examples include crotamiton; N-methylpyrrolidone; polyalkylene glycols such as polyethylene glycol (PEG) and polybutylene glycol; fatty acid esters such as isopropyl myristate and diethyl adipate; oxyalkylene fatty acid esters such as polyethyleneglycol monostearate; fatty acid esters such as polyoxyalkylenesorbitan fatty acid esters; polyoxyethylene hydrogenated castor oil; and surfactants such as polysorbate 80. These dissolving aids may be used alone or in combinations of two or more.

The content of the dissolving aid is preferably 0.1 to 10 mass %, based on the mass of the plaster layer.

The humectant is not particularly restricted so long as it can suppress evaporation of water from the plaster layer with the passage of time. Examples of humectants include polyhydric alcohols such as concentrated glycerin, sorbitol, ethylene glycol, propylene glycol, polyethylene glycol, liquid paraffin, 1,3-propanediol and 1,4-butanediol. These humectants may be used alone or in combinations of two or more. The humectant is preferably concentrated glycerin.

The content of the humectant is preferably 20 to 40 mass %, based on the mass of the plaster layer.

Examples of fresheners include thymol, l-menthol, dl-menthol, l-isopulegol and peppermint oil, among which l-menthol is preferred for use.

The content of the freshener is preferably 0.5 to 3 mass %, based on the mass of the plaster layer.

Examples of stabilizers include oxybenzone, dibutylhydroxytoluene (BHT), sodium edetate and UV absorbers (for example, dibenzoylmethane derivatives).

The gel patch may also comprise a release liner. The release liner is laminated on the plaster layer, on the side opposite the support. If a release liner is provided, it will be possible to inhibit reduction in the water content of the plaster layer during storage, tending to help reduce adhesion of dirt and the like onto the plaster layer.

There are no particular restrictions on the material of the release liner, and the liner used may be one that is generally used by those skilled in the art. When a woven fabric, nonwoven fabric, knitted fabric or resin film is used as the support, the material may be, for example, polyethylene, polypropylene, polybutylene, polyethylene terephthalate, rayon or polyurethane, any of which may be used alone or in combinations of two or more. The material of the release liner is preferably a polypropylene film.

The gel patch may be stored inside a pouch. Storage inside a pouch can minimize reduction in the water content of the plaster layer and can reduce adhesion of dirt and the like onto the plaster layer.

The mass of the plaster layer of the gel patch may be 214 to 1000 g/m$^2$, 400 to 1000 g/m$^2$ or even 400 to 650 g/m$^2$, for example. It is preferably 400 to 650 g/m$^2$ to provide a more satisfactory fitted feel and to allow the adhesion to be improved for longer periods. If the mass of the plaster layer is within this range, it will be possible to reduce the thickness of the gel patch as a whole, helping it to follow the skin while also reducing the level difference with the perimeter sections during attachment, and thereby tending to minimize peeling.

In particular, as mentioned above, when the gel patch is mixed to a mass ratio of neutralized polyacrylic acid:poly (methyl acrylate/2-ethylhexyl acrylate) emulsion:water=1: 2.5-7:7 to 16, and especially when the gel patch has the neutralized polyacrylic acid, poly(methyl acrylate/2-ethylhexyl acrylate) emulsion and water mixed in a mass ratio of neutralized polyacrylic acid:poly(methyl acrylate/2-ethylhexyl acrylate) emulsion:water=1:2.5-7:5-16, the water in the plaster will tend to volatilize more readily and the adhesive force will tend to be reduced when the plaster mass is less than 400 g/m$^2$, and therefore the plaster mass is preferably 400 g/m$^2$ or greater.

The gel patch can be obtained by mixing the neutralized polyacrylic acid, an amount of the poly(methyl acrylate/2-ethylhexyl acrylate) emulsion of at least 2.5 times the mass of the neutralized polyacrylic acid, and water, adding the other components mentioned above, as necessary, to obtain a water-containing plaster, and then evenly spreading the water-containing plaster onto the release liner and laminating the support over it, releasing the release liner to form a plaster layer on the support.

The gel patch described above can maintain adequate adhesive force even after elapse of long periods following application, and the adhesive force can be measured, for example, based on the adhesion score and peel strength, described below. The adhesion score is preferably 75 or greater.

EXAMPLES

The gel patch of the invention will now be explained in greater detail using examples and test examples, with the understanding that the invention is in no way limited to the examples. The contents listed in Table 1 to 12 are expressed as mass %, unless otherwise specified. The method of preparing the gel patches and the method of measuring the adhesive force in the examples and comparative examples were as follows.

(Method of Preparing Gel Patch)

The necessary components are stirred and mixed for a prescribed period of time to obtain a plaster. The obtained plaster is evenly spread onto the release liner so that the plaster mass is 5 g per gel patch (140 mm×100 mm), and then a nonwoven fabric is immediately laminated over it to prepare a gel patch.

Comparative Example 1

Time-Dependent Change in Adhesive Force in a Conventional Gel Patch (1) Test Sample The components listed in Table 1 were stirred and mixed for a prescribed period of time to obtain a plaster. The obtained plaster was evenly spread onto the release liner so that the plaster mass was 5 g per gel patch (140 mm×100 mm). After spreading, a nonwoven fabric was immediately laminated over it to prepare a gel patch (Comparative Example 1).

TABLE 1

| Component name | Content (mass %) |
| --- | --- |
| Glycol salicylate | 2.0 |
| Menthol | 1.0 |
| Gelatin | 2.5 |
| Synthetic aluminum silicate | 1.0 |
| Polyvinyl alcohol | 2.5 |
| Partially neutralized polyacrylic acid | 4.0 |
| Concentrated glycerin | 40.0 |
| Purified water | 44.4 |
| Polyacrylic acid | 2.0 |
| Other components | Remainder |
| Total | 100.0 |

(2) Test Method

Figure 1:
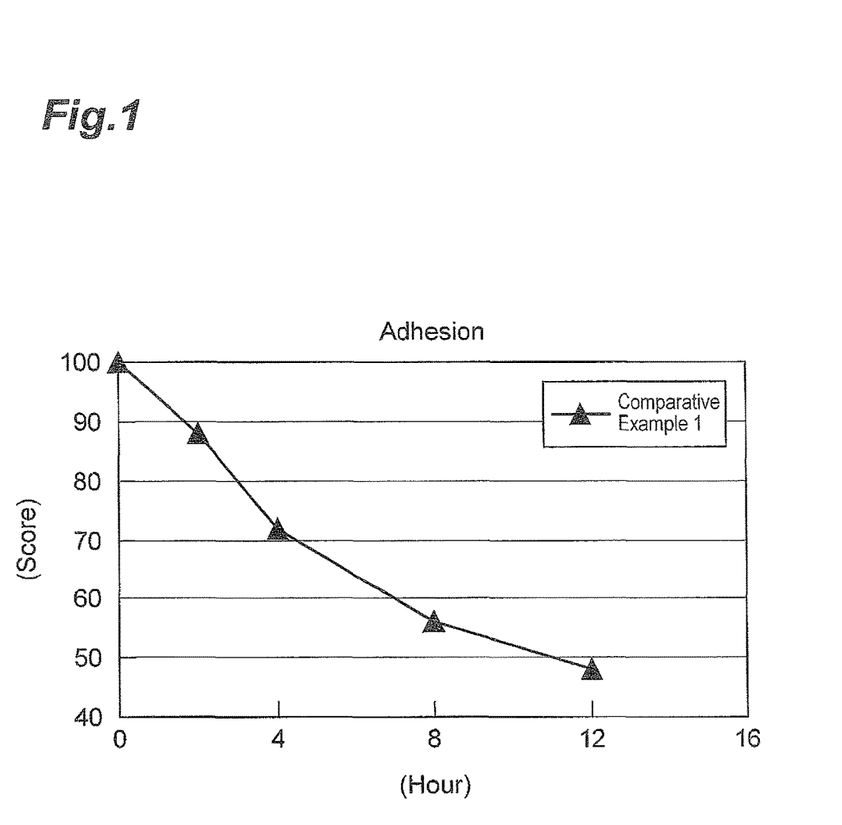
FIG. 1 is a graph showing the time-dependent change in adhesive force of the gel patch produced in Comparative Example 1.

The obtained gel patch was applied onto the knees of 10 subjects, the attached condition of the gel patch after 0 (immediately after application), 2, 4, 8 and 12 hours was evaluated as the adhesion score based on the following evaluation scale, and the average value was calculated.
Evaluation Scale
100: No peeling of preparation
80: Peeling of edges of preparation
60: Peeling of the preparation over ¼ of the application area on the skin
40: Peeling of the preparation over ⅓ of the application area on the skin
20: Peeling of the preparation over ½ of the application area on the skin
0: Sloughing of the preparation
(3) Test Results As shown in FIG. 1, the adhesive force in Comparative Example 1 decreased with the passage of time. The adhesion score in Comparative Example 1 was 100 immediately after application, and the adhesion score fell by approximately 50% after 12 hours following application.

Example 1

Figure 2:
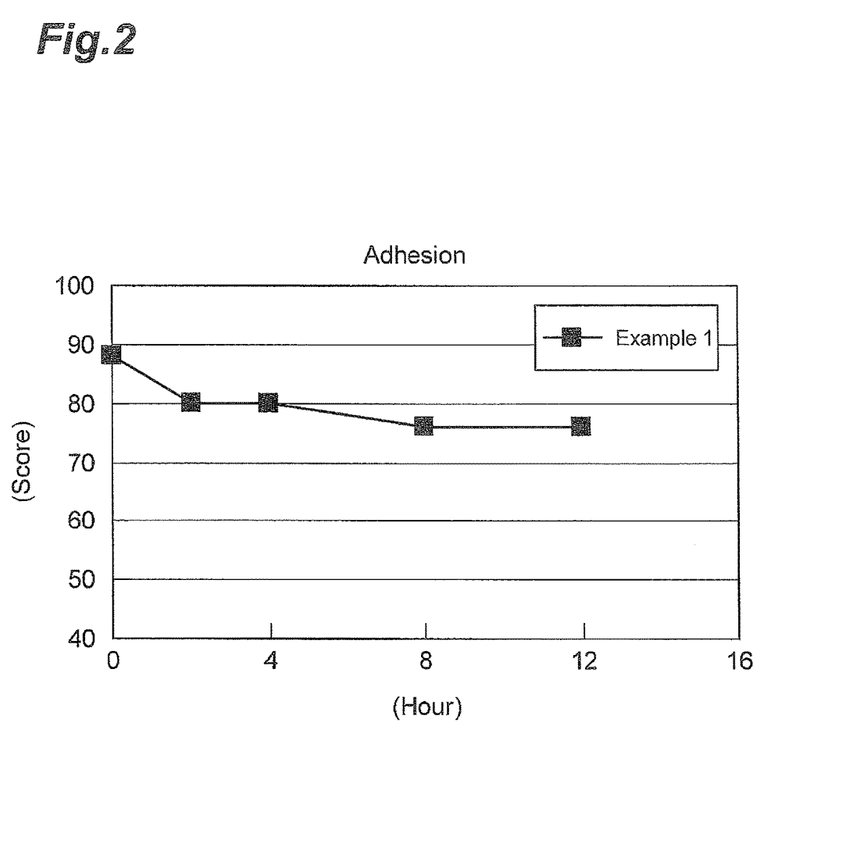
FIG. 2 is a graph showing the time-dependent change in adhesive force of the gel patch produced in Example 1.

Time-Dependent Change in Adhesive Force of Gel Patch Comprising Fully Neutralized Polyacrylic Acid and Methyl Acrylate/2-Ethylhexyl Acrylate Copolymer Emulsion (1) Test Sample A gel patch (Example 1) was prepared in the same manner as Comparative Example 1, except that instead of partially neutralized polyacrylic acid there was used fully neutralized polyacrylic acid (trade name: VISCOMATE F480SS by Showa Denko K.K.), and methyl acrylate/2-ethylhexyl acrylate copolymer resin emulsion (trade name: NIKASOL TS-620 by Nippon Carbide Industries Co., Inc.) was added to 16.7 mass %, the amount of glycerin was 30 mass % and the amount of purified water was 37.8 mass %.
(2) Test Method A test was conducted by the same method as Comparative Example 1.
(3) Test Results As shown in FIG. 2, the adhesion score in Comparative Example 2 was 90 immediately after application, and the adhesion score fell by approximately 10% after 12 hours following application.

Example 2

Figure 3:
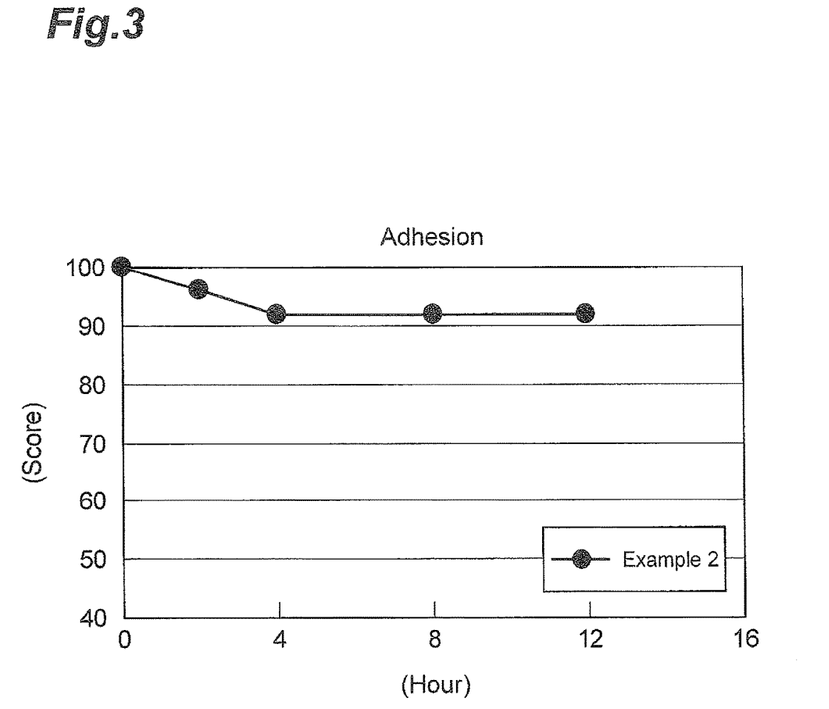
FIG. 3 is a graph showing the time-dependent change in adhesive force of the gel patch produced in Example 2.

Time-Dependent Change in Adhesive Force of Gel Patch Comprising Partially Neutralized Polyacrylic Acid and Methyl Acrylate/2-Ethylhexyl Acrylate Copolymer Emulsion (1) Test Sample A gel patch (Example 2) was obtained in the same manner as Comparative Example 1, except that methyl acrylate/2-ethylhexyl acrylate copolymer (trade name: NIKASOL TS-620 by Nippon Carbide Industries Co., Inc.) was added to 16.7 mass %, the amount of glycerin was 30 mass % and the amount of purified water was 37.8 mass %.
(2) Test Method A test was conducted by the same method as Comparative Example 1.
(3) Test Results As shown in FIG. 3, the adhesion score in Example 1 was 100 immediately after application, and the adhesion score fell by approximately 9% after 12 hours following application. The adhesion score in Example 1 did not fall between 4 hours and 12 hours following application.

Examples 1 and 2, Comparative Example 1

The change in adhesive force of the gel patch with respect to the water content of the plaster layer was measured in the following manner.

(1) Test Sample

The test was conducted for Examples 1 and 2 and Comparative Example 1.

(2) Test Method

The test was conducted by the same method as in Example 1, simultaneously measuring the water content in the preparation.

(3) Test Results

Figure 4:
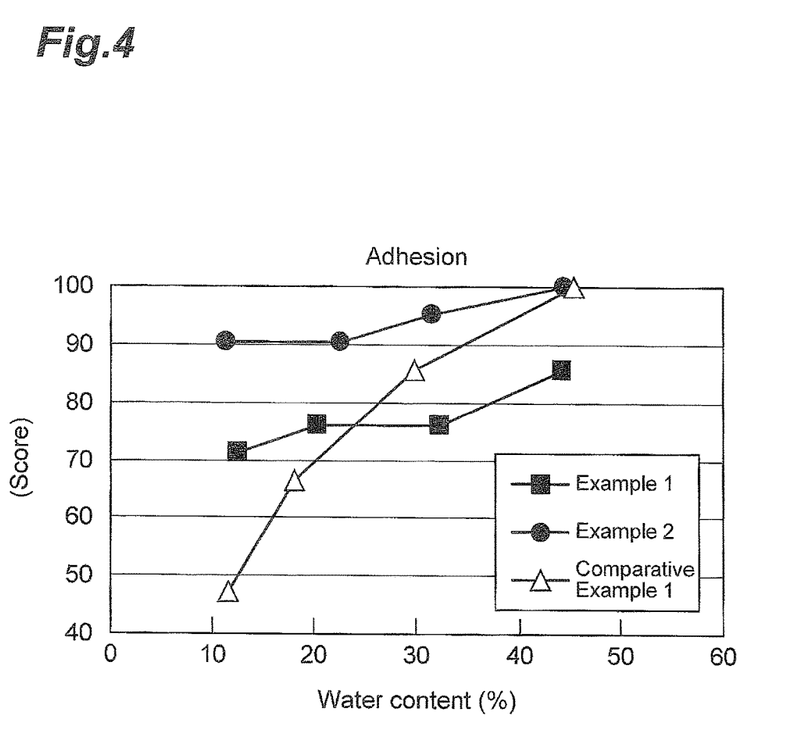
FIG. 4 is a graph showing the relationship between adhesive force and water content for the gel patches produced in Examples 1 and 2 and Comparative Example 1.

As shown in FIG. 4, in Comparative Example 1 the adhesive force continued to fall as the water content of the plaster layer decreased, while in Example 1 and Example 2, no significant fall in adhesive force was seen even with decreasing water content of the plaster layer. This demonstrated that when a poly(methyl acrylate/2-ethylhexyl acrylate) emulsion is added to the plaster layer, the pressure-sensitive adhesive force of the poly(methyl acrylate/2-ethylhexyl acrylate) emulsion is a contributing factor when the water content is low.

Comparative Examples 2, 3 and 4

The change in adhesive force, with respect to the changes in concentration of the partially neutralized polyacrylic acid, poly(methyl acrylate/2-ethylhexyl acrylate) emulsion and water in the gel patch, was measured in the following manner.

(1) Test Sample

The components listed in Table 2 were stirred and mixed for a prescribed period of time to obtain a plaster. The obtained plaster was evenly spread onto the release liner so that the plaster mass was 5 g per gel patch (140 mm×100 mm). After spreading, a nonwoven fabric was immediately laminated over it to prepare a gel patch (Comparative Examples 2 to 4).

TABLE 2

| Component name | Comparative Example 2 | Comparative Example 3 | Comparative Example 4 |
|---|---|---|---|
| Partially neutralized polyacrylic acid | 6.0 | 6.0 | 6.0 |
| Glycerin | 30.0 | 29.0 | 20.0 |
| NIKASOL TS-620 | 0.0 | 1.0 | 10.0 |
| Purified water | 63.9 | 63.9 | 63.9 |
| Other components | 0.1 | 0.1 | 0.1 |
| Total | 100.0 | 100.0 | 100.0 |

(2) Test Method

The gel patches (Comparative Examples 2 to 4) were observed after application for 12 hours. Also, the water content of each gel patch (Comparative Examples 2 to 4) was measured after elapse of a prescribed period of time following application, and the concentrations of the partially neutralized polyacrylic acid and NIKASOL TS-620 in the gel patch at different time points were calculated. In Tables 3 to 5, the "Adhesion" row values are "+" for an adhesion score of 75 or greater, and "−" for a score of less than 75.

(3) Test Results

The results for the gel patches (Comparative Examples 2 to 4) are shown in Tables 3 to 5. The results in Tables 3 and 4 indicate that when the water of the plaster layer is at least 4 times the mass of the partially neutralized polyacrylic acid, an adhesion score of 70 or greater is maintained for the gel patch.

TABLE 3

| | Application time (hr) | 0 | 1 | 7 | 4 | 8 |
|---|---|---|---|---|---|---|
| Concentration | Water | 63.9 | 55.5 | 44.9 | 21.5 | 18.9 |
| | NIKASOL TS-620 | 0 | 0 | 0 | 0 | 0 |
| | Partially neutralized polyacrylic acid | 6 | 7.4 | 9.2 | 13.1 | 13.5 |
| | Glycerin | 30 | 37.3 | 46.1 | 65.8 | 68 |
| | Adhesion score | 92 | 84 | 80 | 64 | 56 |
| | Adhesion | + | + | + | − | − |
| | Water:partially neutralized polyacrylic acid | 10.6:1 | 7.9:1 | 5:1 | 1.6:1 | 1.5:1 |
| | Water:NIKASOL TS-620 | 0 | 0 | 0 | 0 | 0 |
| | Partially neutralized polyacrylic acid:NIKASOL TS-620 | 1:0 | 1:0 | 1:0 | 1:0 | 1:0 |

TABLE 4

| | Application time (hr) | 0 | 1 | 2 | 4 | 8 |
|---|---|---|---|---|---|---|
| Concentration | Water | 63.9 | 53.9 | 42.3 | 22.9 | 22.6 |
| | NIKASOL TS-620 | 1.0 | 1.3 | 1.6 | 2.1 | 2.1 |
| | Partially neutralized polyacrylic acid | 6 | 7.7 | 9.6 | 12.8 | 12.9 |
| | Glycerin | 29 | 36.6 | 45.9 | 61.3 | 61.5 |
| | Adhesion score | 92 | 76 | 72 | 68 | 56 |
| | Adhesion | + | + | − | − | − |
| | Water:partially neutralized polyacrylic acid | 10.6:1 | 7:1 | 4.4:1 | 1.8:1 | 1.8:1 |
| | Water:NIKASOL TS-620 | 64:1 | 42:1 | 26:1 | 11:1 | 11:1 |
| | Partially neutralized polyacrylic acid:NIKASOL TS-620 | 6:1 | 5.9:1 | 6:1 | 6.1:1 | 6.1:1 |

TABLE 5

| | Application time (hr) | 0 | 1 | 2 | 4 | 8 |
|---|---|---|---|---|---|---|
| Concentration | Water | 63.9 | 54.7 | 43.2 | 22.5 | 18.1 |
| | NIKASOL TS-620 | 10 | 12.5 | 15.7 | 21.5 | 22.7 |

TABLE 5-continued

| Application time (hr) | 0 | 1 | 2 | 4 | 8 |
|---|---|---|---|---|---|
| Partially neutralized polyacrylic acid | 6 | 7.5 | 9.4 | 12.9 | 13.6 |
| Glycerin | 20 | 27.8 | 37.4 | 54.8 | 58.4 |
| Adhesion score | 96 | 92 | 88 | 80 | 72 |
| Adhesion | + | + | + | + | − |
| Water:partially neutralized polyacrylic acid | 10.6:1 | 7.3:1 | 4.6:1 | 1.7:1 | 1.3:1 |
| Water:NIKASOL TS-620 | 6.4:1 | 4.4:1 | 2.8:1 | 1:1 | 0.7:1 |
| Partially neutralized polyacrylic acid:NIKASOL TS-620 | 0.6:1 | 0.6:1 | 0.6:1 | 0.6:1 | 0.6:1 |

Examples 3 and 4, Comparative Example 5

Relationship Between Mixing Ratio of Partially Neutralized Polyacrylic Acid and Methyl Acrylate/2-Ethylhexyl Acrylate Copolymer Emulsion, and Peel Strength after 8 Hours (1) Test Sample The components listed in Table 6 were stirred and mixed for a prescribed period of time to obtain a plaster. The obtained plaster was evenly spread onto the release liner so that the plaster mass was 5 g per gel patch (140 mm×100 mm). After spreading, a nonwoven fabric was immediately laminated over it to prepare a gel patch (Comparative Example 5 and Examples 3 and 4).

TABLE 6

| Component name | Comparative Example 5 | Example 3 | Example 4 |
|---|---|---|---|
| Partially neutralized polyacrylic acid | 3.00 | 3.00 | 3.00 |
| Polyacrylic acid | 3.00 | 3.00 | 3.00 |
| NIKASOL TS-620 | 5.00 | 10.00 | 20.00 |
| Concentrated glycerin | 30.00 | 30.00 | 24.00 |
| Purified water | 49.95 | 47.95 | 43.95 |
| Other components | Remainder | Remainder | Remainder |
| Total | 100.00 | 100.00 | 100.00 |

(2) Test Method

A poultice was cut out into a 2 cm×7.5 cm rectangle, the release liner was removed and the poultice was attached to a polyethylene plate and allowed to stand for 8 hours under conditions with a temperature of 25° C. and a humidity of 60%. Next, the poultice was detached at a rate of 30 cm/min, and the load (N) was measured at the points where the leading detachment edge of the poultice moved 20, 40, 60, 80 and 100 mm. The measurement was repeated 3 times, and the average value for the obtained loads was calculated and recorded as the peel test value after 8 hours.

(3) Test Results

Figure 5:
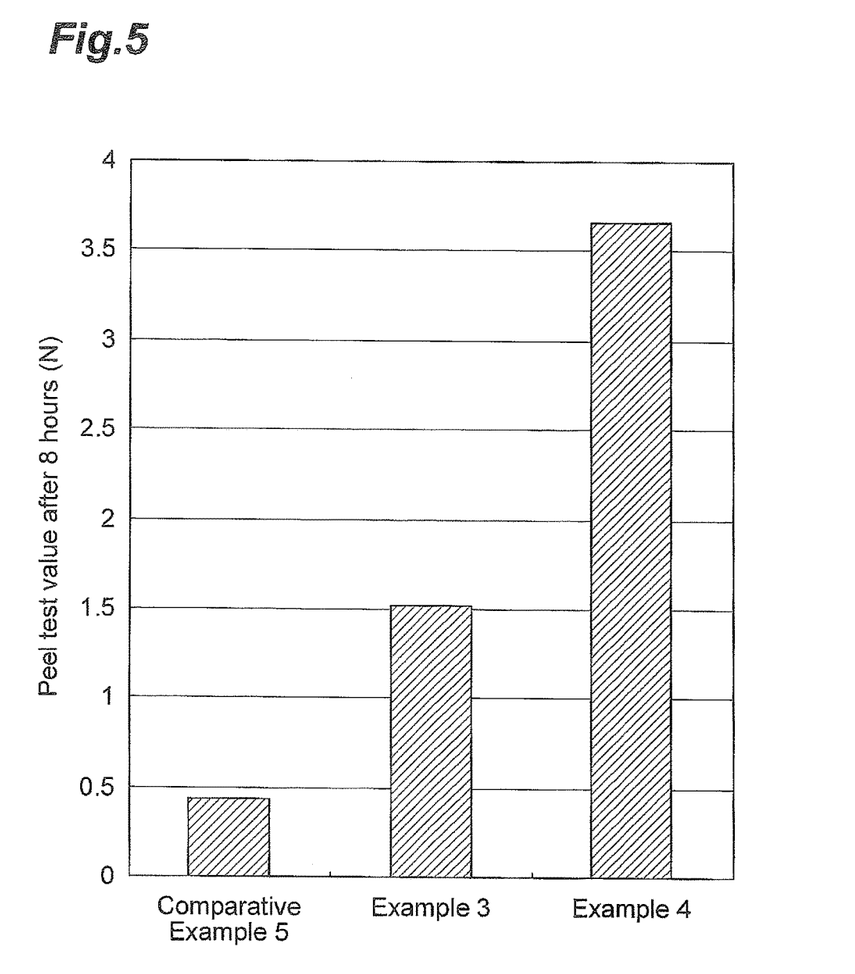
FIG. 5 is a graph showing the peel strengths of the gel patches produced in Examples 3 and 4 and Comparative Example 5, after 8 hours.

As shown in FIG. 5, Examples 3 and 4 exhibited a level of adhesive force at least twice that of Comparative Example 5. Even with the gel patch wherein the content of the partially neutralized polyacrylic acid is 5% based on the mass of the gel patch as a whole, high adhesive force was exhibited when the mass of the NIKASOL TS-620 was 2.5 times or greater compared to the mass of the partially neutralized polyacrylic acid.

Example 5 and Comparative Example 6

(1) Test Sample

The components listed in Table 7 were mixed to prepare a plaster for a gel patch. The obtained plaster was spread onto a plastic film (release liner) to 7 g each (14 cm×10 cm), and after laminating a nonwoven fabric (support) over it, it was appropriately cut to prepare gel patches for Comparative Example 6 and Example 5.

TABLE 7

| | Comparative Example 6 | Example 5 |
|---|---|---|
| Partially neutralized polyacrylic acid | 3.0 | 3.0 |
| Polyacrylic acid | 3.0 | 3.0 |
| NIKASOL TS-620 | 6.0 | 7.5 |
| Gelatin | 2.5 | 2.5 |
| Polyvinyl alcohol | 2.5 | 2.5 |
| Concentrated glycerin | 20.0 | 20.0 |
| Glycol salicylate | 2.0 | 2.0 |
| Purified water | 57.45 | 55.95 |
| Other components | 3.55 | 3.55 |
| Total | 100 | 100 |

(2) Method for Test 1

Each obtained gel patch was applied onto the elbow of 15 subjects, and the adhesion score was evaluated by the state of adhesion of the gel patch, based on the following evaluation scale Evaluation Scale 100: No peeling of preparation 80: Peeling of edges of preparation 60: Peeling of the preparation over ¼ of the application area on the skin 40: Peeling of the preparation over ⅓ of the application area on the skin 20: Peeling of the preparation over ½ of the application area on the skin 0: Sloughing of the preparation (3) Results for Test 1

Figure 6:
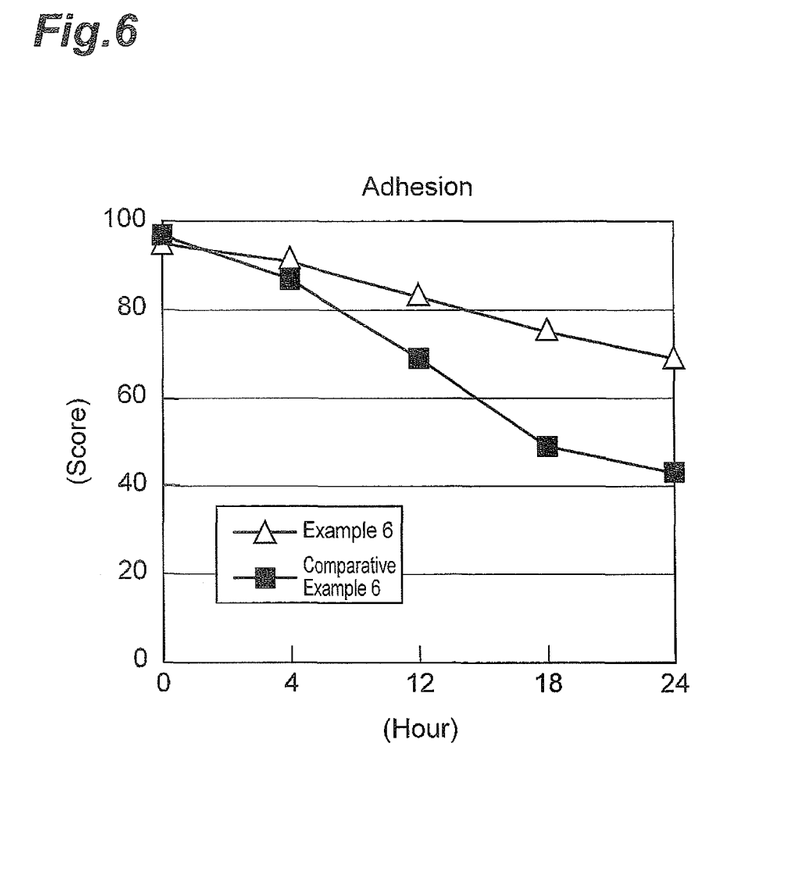
FIG. 6 is a graph showing the time-dependent change in adhesive force of the gel patches produced in Example 6 and Comparative Example 6.

The evaluation results for the human skin adhesion test are shown in Table 8 and FIG. 6. The adhesion score for the gel patch of Comparative Example 6 was below 70 after 12 hours following application, and below 50 after 18 hours. On the other hand, the adhesion score for the gel patch of Example 5 was approximately 70 even after 24 hours following application.

TABLE 8

| Elapsed time [hr] | Comparative Example 6 | Example 5 |
|---|---|---|
| 0 | 97 | 95 |
| 4 | 87 | 91 |
| 12 | 69 | 83 |
| 18 | 49 | 75 |
| 24 | 43 | 69 |

(4) Method for Test 2

The gel patches of Comparative Example 6 and Example 5 were set on an experiment table at room temperature (temperature: 25° C., relative humidity: 60%), with the plaster layers contacting, and the change in mass of the gel patches with the passage of time was examined.

(5) Results for Test 2

Table 9 shows the results of measuring the overall masses of the gel patches of Comparative Example 6 and Example 5. Both had approximately the same rate of mass reduction.

TABLE 9

| Elapsed time [hr] | Comparative Example 6 | Example 5 |
|---|---|---|
| 0 | 6.81 | 6.85 |
| 4 | 4.61 | 4.70 |
| 18 | 3.46 | 3.64 |
| 24 | 3.45 | 3.63 |

The time-dependent changes in mass of each component of the gel patches of Comparative Example 6 and Example 5 are shown in Tables 10 and 11. Based on the results for the gel patch of Example 5 after 4 hours following application, it is seen that the purified water mass was approximately 7.5 times the mass of the partially neutralized polyacrylic acid, and adhesion was continuously maintained for 20 hours thereafter. Moreover, based on the results for the gel patch of Example 5 after 18 hours following application, it is seen that the purified water mass was approximately 2 times the mass of the partially neutralized polyacrylic acid, and adhesion was continuously maintained for 6 hours thereafter. On the other hand, based on the results for the gel patch of Comparative Example 6, when the content ratio between the partially neutralized polyacrylic acid and NIKASOL TS-620 was 1:2, the adhesion fell as the water content decreased.

TABLE 10

| | Elapsed time [time] | | | |
|---|---|---|---|---|
| | 0 | 4 | 18 | 24 |
| Partially neutralized polyacrylic acid | 3.0 | 4.57 | 6.29 | 6.32 |

TABLE 10-continued

| | Elapsed time [time] | | | |
|---|---|---|---|---|
| | 0 | 4 | 18 | 24 |
| Polyacrylic acid | 3.0 | 4.57 | 6.29 | 6.32 |
| NIKASOL TS-620 | 6.0 | 9.14 | 12.58 | 12.63 |
| Gelatin | 2.5 | 3.81 | 5.24 | 5.26 |
| Polyvinyl alcohol | 2.5 | 3.81 | 5.24 | 5.26 |
| Concentrated glycerin | 20.0 | 30.47 | 41.93 | 42.10 |
| Glycol salicylate | 2.0 | 3.05 | 4.19 | 4.21 |
| Purified water | 57.45 | 35.18 | 10.79 | 10.43 |
| Other components | 3.55 | 5.40 | 7.45 | 7.47 |
| Total | 100 | 100 | 100 | 100 |

TABLE 11

| | Elapsed time [time] | | | |
|---|---|---|---|---|
| | 0 | 4 | 18 | 24 |
| Partially neutralized polyacrylic acid | 3.0 | 4.50 | 5.97 | 5.98 |
| Polyacrylic acid | 3.0 | 4.50 | 5.97 | 5.98 |
| NIKASOL TS-620 | 7.5 | 11.25 | 14.91 | 14.96 |
| Gelatin | 2.5 | 3.75 | 4.97 | 4.99 |
| Polyvinyl alcohol | 2.5 | 3.75 | 4.97 | 4.99 |
| Concentrated glycerin | 20.0 | 30.00 | 39.77 | 39.90 |
| Glycol salicylate | 2.0 | 3.00 | 3.98 | 3.99 |
| Purified water | 55.95 | 33.92 | 12.40 | 12.13 |
| Other components | 3.55 | 5.33 | 7.06 | 7.08 |
| Total | 100 | 100 | 100 | 100 |

Examples 6 to 13

The components listed in Table 12 were mixed to prepare a plaster for a gel patch. Each mixture was spread onto a polyethylene terephthalate knitted fabric to 500 g/m² to obtain a gel patch (Examples 6 to 13). The gel patches exhibited highly satisfactory adhesion even after 8 hours of application.

TABLE 12

| Component | Example 6 | Example 7 | Example 8 | Example 9 | Example 10 | Example 11 | Example 12 | Example 13 |
|---|---|---|---|---|---|---|---|---|
| Ketoprofen | 2 | 2 | 2 | 2 | — | — | — | — |
| Felbinac | — | — | — | — | 1 | — | — | — |
| Diclofenac sodium | — | — | — | — | — | 1 | — | — |
| Loxoprofen sodium | — | — | — | — | — | — | 1 | — |
| Glycol salicylate | — | — | — | — | — | — | — | 2 |
| Tocopherol acetate ester | — | — | — | — | — | — | — | 1 |
| Oxybenzone | — | — | 1 | — | — | — | — | — |
| BHT | — | — | — | — | — | 0.1 | — | — |
| L-Menthol | 2 | 2 | 0.5 | 0.5 | 1 | 0.5 | — | 1 |
| Crotamiton | 2.5 | 2.5 | 2.5 | 2 | 1.5 | 1 | 0.5 | — |
| Peppermint oil | — | — | — | — | — | — | 1 | — |
| Isopropyl myristate | — | — | — | — | 1 | — | — | — |
| Titanium oxide | — | — | — | — | — | 1 | 1 | — |
| Gelatin | 2.5 | 2.5 | 2.5 | 2.5 | 2.5 | 2.5 | — | 2.5 |
| Partially neutralized polyacrylic acid | 4 | 4 | 5 | 5 | 4 | 2.5 | 3 | 3 |
| Carmellose sodium | — | — | — | — | — | 4 | 5 | — |
| Polyvinyl alcohol | 2.5 | 2.5 | 2.5 | 2 | 2 | — | — | 3.5 |
| Polyacrylic acid | 2 | 2 | 1 | 2 | 3 | 3 | 1 | 4 |
| Concentrated glycerin | 15 | 20 | 30 | 15 | 20 | 25 | 30 | 27 |
| Propylene glycol | 15 | 5 | — | 15 | 10 | 10 | — | — |
| NIKASOL TS-620 | 17 | 17 | 12.5 | 17 | 10 | 8.4 | 12.5 | 8.5 |
| PEG monostearate | 0.5 | — | — | 0.5 | — | — | — | — |

TABLE 12-continued

| Component | Example 6 | Example 7 | Example 8 | Example 9 | Example 10 | Example 11 | Example 12 | Example 13 |
|---|---|---|---|---|---|---|---|---|
| Polyoxyethylene hydrogenated castor oil | — | 0.5 | — | — | 0.5 | — | — | 0.5 |
| Polysorbate 80 | — | — | 0.5 | — | — | 0.5 | 0.5 | — |
| Sodium edetate | — | — | 0.2 | 0.1 | 0.1 | 0.3 | 0.2 | — |
| Other components | 1 | 1 | 1 | 2 | 1 | 1 | 1.5 | 1 |
| Purified water | 34 | 39 | 38.8 | 34.4 | 42.4 | 39.2 | 43.3 | 46 |
| Total | 100 | 100 | 100 | 100 | 100 | 100 | 100 | 100 |

In addition, for Examples 6, 10 and 13 there were prepared gel patches comprising plaster layers at 3 g (214 g/m$^2$), 5 g (357 g/m$^2$), 6 g (429 g/m$^2$), 7 g (500 g/m$^2$) or 14 g (1000 g/m$^2$) per 140 cm$^2$ application area of the plaster.

The pH value was 5 for the gel patches of Examples 1 to 13, and no seepage of water was observed from the plaster layer into the support. Likewise, no seepage was observed even when production was such for a pH of 6.5.

There were also prepared gel patches using a woven fabric, nonwoven fabric or foamed sheet as the support, having plaster layers with the same compositions as Examples 1 to 13 and basis weights of 100 g/m$^2$.

The invention claimed is:

1. A gel patch, comprising:
a plaster layer on a support, the plaster layer comprising:
a mixture of at least a neutralized polyacrylic acid, a poly(methyl acrylate/2-ethylhexyl acrylate) emulsion, and water, wherein the poly(methyl acrylate/2-ethylhexyl acrylate) emulsion comprises poly(methyl acrylate/2-ethylhexyl acrylate) and water as a medium, wherein the poly(methyl acrylate/2-ethylhexyl acrylate) emulsion is an emulsion having an evaporation residue of 57 to 61% at or above the boiling point of the medium and is present in an amount ranging between 2.5 times and 10 times inclusive a mass of the neutralized polyacrylic acid; and
a polyacrylic acid in the amount of 1-5 mass % based on the total mass of the plaster layer, wherein the neutralized polyacrylic acid present in the plaster layer is 1 to 6 mass %, based on a total mass of the plaster layer;
wherein the gel patch has an adhesive force based on an adhesive force of the poly(methyl acrylate/2-ethylhexyl acrylate) in the poly(methyl acrylate/2-ethylhexyl acrylate) emulsion and an adhesive force of the neutralized polyacrylic acid, and
wherein upon application, the adhesive force of the neutralized polyacrylic acid is greater than the adhesive force of the poly(methyl acrylate/2-ethylhexyl acrylate), and the adhesive force of the poly(methyl acrylate/2-ethylhexyl acrylate) increases to become greater than the adhesive force of the neutralized polyacrylic acid as the amount of water in the plaster layer is reduced.

2. The gel patch according to claim 1, wherein the poly(methyl acrylate/2-ethylhexyl acrylate) emulsion comprises poly(oxyethylene)nonylphenyl ether.

3. The gel patch according to claim 1, wherein the neutralized polyacrylic acid is partially neutralized polyacrylic acid.

4. The gel patch according to claim 1, wherein the water present in the plaster layer is greater by mass than the poly(methyl acrylate/2-ethylhexyl acrylate) emulsion present in the plaster layer.

5. The gel patch according to claim 1, wherein the water present in the plaster layer is at least 4 times greater by mass than the neutralized polyacrylic acid present in the plaster layer.

6. The gel patch according to claim 1, wherein the neutralized polyacrylic acid, the poly(methyl acrylate/2-ethylhexyl acrylate) emulsion and the water are mixed in a mass ratio of neutralized polyacrylic acid:poly(methyl acrylate/2-ethylhexyl acrylate) emulsion:water=1:2.5-7:5-16.

7. The gel patch according to claim 6, wherein the mass ratio of neutralized polyacrylic acid:poly(methyl acrylate/2-ethylhexyl acrylate) emulsion:water=1:2.5-7:7-16.

8. The gel patch according to claim 1, wherein the water present in the plaster layer is 20 to 60 mass % of a total mass of the plaster layer.

9. The gel patch according to claim 1, wherein a plaster layer mass is 214 to 1000 g/m$^2$.

10. The gel patch according to claim 1, wherein the amount of water in the plaster layer is reduced by evaporation.

11. A method of producing a gel patch according to claim 1, having an adhesive force and comprising a plaster layer on a support, the method comprising: mixing water, a neutralized polyacrylic acid, a polyacrylic acid, and a poly(methyl acrylate/2-ethylhexyl acrylate) emulsion, wherein the poly(methyl acrylate/2-ethylhexyl acrylate) emulsion is in an amount ranging between 2.5 times and 10 times inclusive a mass of the neutralized polyacrylic acid to obtain the plaster layer, wherein the adhesive force of the gel patch can be maintained even with a reduction of water content.

12. The gel patch according to claim 2, wherein the neutralized polyacrylic acid is partially neutralized polyacrylic acid.

13. The gel patch according to claim 2, wherein the water present in the plaster layer is greater by mass than the poly(methyl acrylate/2-ethylhexyl acrylate) emulsion present in the plaster layer.

14. The gel patch according to claim 3, wherein the water present in the plaster layer is greater by mass than the poly(methyl acrylate/2-ethylhexyl acrylate) emulsion present in the plaster layer.

15. The gel patch according to claim 2, wherein the water present in the plaster layer is at least 4 times greater by mass than the neutralized polyacrylic acid present in the plaster layer.

16. The gel patch according to claim 3, wherein the water present in the plaster layer is at least 4 times greater by mass than the neutralized polyacrylic acid present in the plaster layer.

17. The gel patch according to claim 4, wherein the water present in the plaster layer is at least 4 times greater by mass than the neutralized polyacrylic acid present in the plaster layer.

18. The gel patch according to claim 2, wherein the neutralized polyacrylic acid, the poly(methyl acrylate/2- ethylhexyl acrylate) emulsion and the water are mixed in a mass ratio of neutralized polyacrylic acid:poly(methyl acrylate/2-ethylhexyl acrylate) emulsion:water=1:2.5-7:5-16.

* * * * *

UNITED STATES PATENT AND TRADEMARK OFFICE
CERTIFICATE OF CORRECTION

PATENT NO. : 10,369,115 B2
APPLICATION NO. : 14/913455
DATED : August 6, 2019
INVENTOR(S) : Keiichiro Tsurushima et al.

It is certified that error appears in the above-identified patent and that said Letters Patent is hereby corrected as shown below:

On the Title Page

Item (73), please remove the Assignee: "HISAMITSU PHARMACEUTICAL CO., LTD." and replace with "HISAMITSU PHARMACEUTICAL CO., INC."

Signed and Sealed this
Seventh Day of April, 2020

Andrei Iancu
*Director of the United States Patent and Trademark Office*